United States Patent [19]

Bolstad

[11] Patent Number: 4,649,426

[45] Date of Patent: Mar. 10, 1987

[54] ELECTRONIC IMAGING SYSTEM AND TECHNIQUE

[75] Inventor: Jon O. Bolstad, Idaho Falls, Id.

[73] Assignee: The United States of America as represented by the United States Department of Energy, Washington, D.C.

[21] Appl. No.: 619,759

[22] Filed: Jun. 12, 1984

[51] Int. Cl.[4] .................................... H04N 7/18
[52] U.S. Cl. .................... 358/101; 219/137 R
[58] Field of Search .............. 358/93, 107, 101, 108; 356/308–318, 370, 372, 4.5, 5; 219/122, 136, 124, 34, 137 R, 130.01, 130.31, 130.21; 350/276 R

[56] References Cited

U.S. PATENT DOCUMENTS

| | | | |
|---|---|---|---|
| 3,526,748 | 9/1970 | Rienks | 358/101 |
| 3,947,119 | 3/1976 | Bamberg et al. | 356/5 |
| 3,958,078 | 5/1976 | Fowler et al. | 358/106 |
| 4,183,055 | 1/1980 | Burkhardt et al. | 358/101 |
| 4,186,353 | 1/1980 | Boutineau | 350/370 X |
| 4,204,224 | 5/1980 | Buken et al. | 358/107 |
| 4,219,844 | 8/1980 | Ohsumi et al. | 358/101 X |
| 4,225,771 | 9/1980 | Justice et al. | 358/108 X |
| 4,319,270 | 3/1982 | Kimura et al. | 358/101 X |
| 4,410,787 | 10/1983 | Kremers et al. | 358/107 X |
| 4,416,530 | 11/1983 | Hebert et al. | 350/370 |
| 4,493,968 | 1/1985 | Brown | 358/107 X |

FOREIGN PATENT DOCUMENTS 2950657 6/1981 Fed. Rep. of Germany ........... 219/130.31

Primary Examiner—Howard W. Britton
Assistant Examiner—Victor R. Kostak
Attorney, Agent, or Firm—Jeannette M. Walder; Paul A. Gottlieb; Judson R. Hightower

[57] ABSTRACT

A method and system for viewing objects obscurred by intense plasmas or flames (such as a welding arc) includes a pulsed light source to illuminate the object, the peak brightness of the light reflected from the object being greater than the brightness of the intense plasma or flame; an electronic image sensor for detecting a pulsed image of the illuminated object, the sensor being operated as a high-speed shutter; and electronic means for synchronizing the shutter operation with the pulsed light source.

23 Claims, 3 Drawing Figures

ELECTRONIC IMAGING SYSTEM AND TECHNIQUE

CONTRACTURAL ORIGIN OF THE INVENTION

The U.S. States Government has rights in this invention pursuant to Contract No. DE-AC07-76ID01570 between the U.S. Department of Energy and EG&G Idaho, Inc.

BACKGROUND OF THE INVENTION

This invention relates generally to a system and method for viewing objects normally obscured from vision by intense plasmas or flames. The invention is particularly applicable to electric arc welding where details of the welding pool, electrode, weld joint are concealed by the luminescent cloud of the welding plasma.

In both manual and automatic welding, welding quality can be improved by real-time sensory information about a variety of weld site parameters, including diameter and depth of the molten welding pool, temperature gradients around the pool, position of the pool vs the welding seam or previous weld beads, contamination or slag in the welding pool, and the degree of wetting at the weld pool/solidus interface. These parameters and others are observed or inferred in the manual welding process, primarily by means of the welder's vision. Hearing also plays a role in monitoring the dynamics of the welding arc.

A variety of sensory techniques have been used in automatic welding as a replacement for the manual welder's vision. However, as the trend continues towards autogeneous welding (automatic welding free from preprogramming by external sources), the welder's vision cannot be replaced but must instead be duplicated to some degree by the use of electronic vision, small computers, and image processing software. This approach would generally involve the use of a miniature video camera or solid-state optical detector array and appropriate optics which must be carefully integrated into the design of the welding torch.

One current example is the General Electric Weldvision TM system, which was developed by Richard W. Richardson at Ohio State University and commercialized by General Electric. It is designed for the gas-tungsten arc welding process (GTAW) in which a tungsten electrode is used to create the arc and the electrode and weld site are protected from oxidation by use of an inert purge gas. The vertical electrode is enclosed by a tubular shroud (or "gas cup") and the purge gas flows through the shroud from above and onto the welding site. Richardson devised an optical system coaxial with the electrode to acquire an image, which in turn is relayed by a fiberoptic bundle to a small solid-state CID video camera. His viewing geometry is attractive, first, because it provides a direct overhead perspective of the entire welding pool and, secondly, because the welding electrode provides blockage of light from the brightest portion of the welding arc and thereby improves the quality of the video image. This system is used primarily to obtain video data describing weld pool diameter and position relative to the prepared welding groove. The groove location is revealed by two parallel laser stripes beamed onto the weld joint in advance of the welding pool. This system accomplishes true automatic welding, but is limited to single-pass welding because the guidance signature from the groove is destroyed during the first welding pass.

Another welding process, important for its use in heavy construction, is gas-metal arc welding (GMAW). The GMAW process is similar to GTAW, however, the tungsten electrode is replaced by a consumable wire electrode, which provides the filler material for the weld. This process applies metal at higher rates at less power, but creates a greater threat to optical components, with much higher levels of spattering metal.

Therefore, it is an object of the present invention to provide a system and method to generate electronic imagery for automatic control of multiple-pass welding processes.

It is another object of the present invention to provide a system and method for acquiring high-definition imagery of objects obscured by intense plasmas or flames, such as welding sites.

Additional objects, advantages, and novel features of the invention will be set forth in part in the description which follows, and in part will become apparent to those skilled in the art upon examination of the following or may be learned by practice of the invention.

SUMMARY OF THE INVENTION

In accordance with the principles of the present invention there is provided a system for viewing an object obscured by an intense plasma or flame comprising: a pulsed light source for illuminating the object, the peak brightness of the light reflected from the object being greater than the brightness of the intense plasma or flame; an electronic image sensor for detecting a pulsed image of the illuminated object, said sensor being operated as a high speed shutter; and electronic means for synchronizing said shutter operation with said pulsed light source. The invention is based on the premise that, in the case of welding, the welding arc light in the form of an intense plasma or flame, must be greatly suppressed and/or replaced by illumination from an external light source. This is accomplished in part by illuminating the object (welding site) with a pulsed light source such as a short-arc flashlamp or laser. A pulsed image of the illuminated object is detected by an electronic image sensor such as an intensifier tube. Other sensors which may be used include semiconductor integrated circuit image devices and one-dimensional semiconductor array devices. The sensor is operated as a shutter by electronically switching it on and off. In the case of an intensifier tube, this is accomplished with a voltage pulse to its photocathode, which is then synchronized in time with the flash from the pulsed light source. The duration of the photocathode pulse and light pulse are about equivalent and the intensifier tube amplifies the light flash efficiently, while rejecting all of the light emanating continuously from the intense plasma or flame (welding arc), except that which coincides with the photocathode pulse.

Preferably, the pulsed image detected by the intensifier tube is transferred to a video camera. Alternatively, an operator can view the pulsed image directly by placing an optical eye-piece assembly or stereo viewing system at the sensor output. The video camera permits the system to be used with cross-correlation video tracking apparatus, which has been used by the military in recent years for guidance of small tactical missiles. A digital microprocessor may be used to correlate large sections of the video image against similar imagery stored in the computer memory. Tracking information is derived from a collection of image features over a larger image area and there is no dependence on a well-defined single feature (i.e., a weld groove). The same microprocessor would also be used for measurement of weld pool diameter, for detection of contaminants in the pool, and for measurement of wetting angle.

BRIEF DESCRIPTION OF THE DRAWINGS

The present invention is illustrated in the accompanying drawings wherein.

DETAILED DESCRIPTION OF THE INVENTION

Figure 1:
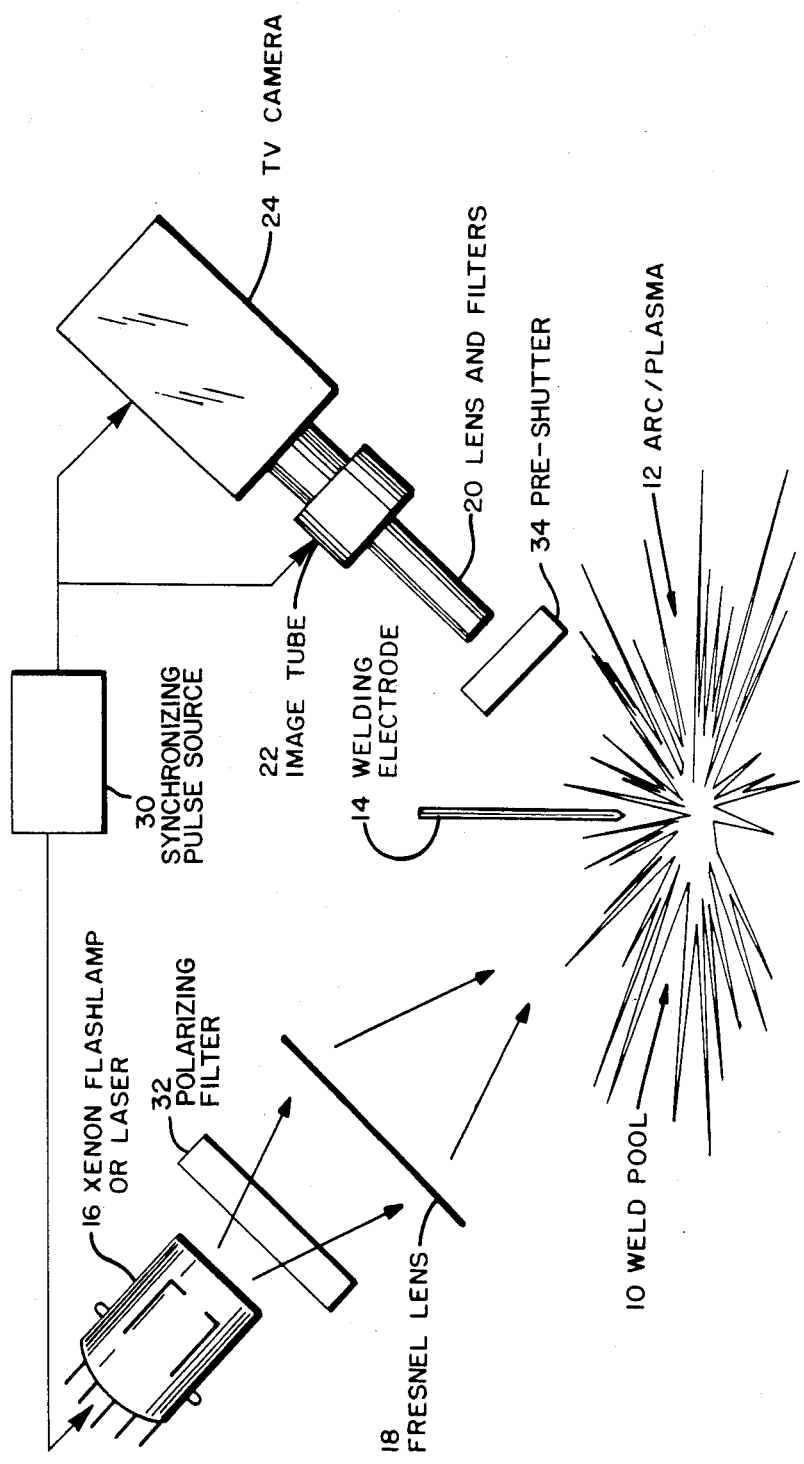
FIG. 1 is a schematic of an electronic imaging system.

A schematic of an electronic imaging system as it might be used to view a welding site is shown in FIG. 1. The imaging system permits weld pool 10 to be viewed so that the welding process can be controlled. The weld pool 10 is obscured by arc (plasma) 12 produced by welding electrode 14. Pulsed light source 16, which may be a xenon flashlamp or laser is used to illuminate the weld pool 10. Optical means 18, which in this case is a fresnel lens, is used to focus the pulsed light to a region below the welding electrode 14. The lens is used to maximize the peak power density of the light pulse from source 16 by restricting the area covered to the weld pool 10 and the immediate, adjacent areas of interest. The illuminated weld pool 10 is viewed by image intensifier tube 22 followed by television camera 24. The illuminated image is projected onto image tube 22 by lens and filters 20. Image tube 22 is equipped with appropriate drive electronics to allow it to function as a very high speed optical shutter. The system operates by synchronizing the shutter electronically with the pulsed light source by means of the synchronizing pulse source 30.

Light source 16 is triggered once per video frame (every 30 milliseconds) or at some multiple thereof. The flash duration is on the order of 3.0 microseconds or less and the gate width of the shutter is approximately equal. The net result is a system which preferentially accepts the light originating from the pulsed light source, but strongly discriminates against the steady state light coming from the welding arc. The degree of discrimination is simply the ratio of the frame interval, $T_f$, to the shutter interval $T_s$, or about 10,000:1 for $T_f$30 milliseconds and $T_s = 3.0$ microseconds. This is because the video camera is a system which normally integrates light for the full 30 millisecond period before readout, but in this case, the integration period is limited to the shutter gate width and the camera, therefore, receives only the very small fraction of welding light generated when the gate is open.

The instantaneous brightness of the welding arc light is exceeded by the peak brightness of the flash energy reflected from the weld site. This ensures that the resultant video image will contain only a small component of light from the arc and plasma. The visibility through the plasma is greatly enhanced and the extreme variability of light level across the weld site is replaced by the relatively uniform and controlled illumination from the pulsed light source. Overall image quality is improved with much more detail and greater contrast.

To protect the sensor from overloads such as those caused by photon saturation or high levels of heat produced by the arc and plasma, a pre-shuttering device 34 may be used. The pre-shuttering device 34 would not have to operate as fast as the shuttering speed of the sensor. The pre-shuttering device prevents heat build-up on the sensor by interrupting the light from the arc and plasma. The pre-shuttering device 34 may be a mechanical shutter, an electro-optically or acoustically driven shutter; or a PLZT ferroelectric ceramic shuttering device.

The relative direction for illumination and viewing of the weld site can be critical. The geometry shown in FIG. 1 (with the light source and sensor being in a plane which is perpendicular to the source of the welding pool) is generally least desirable because the molten welding pool acts as a mirror surface with a highly directional (specular) reflection characteristic. In this case, the camera is positioned to receive a strong specular beam if the weld pool is relatively flat. Generally it is important to minimize or suppress the specular reflection component—as one avoids the glare of the sun from a body a water. This is because structural detail at the welding site is largely revealed by diffusely reflected light from the solid material.

Minimizing specular reflection can be achieved by detecting the pulsed image from an angle which excludes the angle of major specular reflection from the object (for example, in a viewing direction nearly coincident with the direction of illumination). The specular component can also be suppressed by polarizing the pulsed image prior to detection (by use of an optical polarizing filter 20 mounted in the lens housing in front of the intensifier tube 22) or by polarizing the pulsed light source (by placing a cross-polarizing filter 32 in the illumination beam or by using a polarized laser as the light source) or a combination of both. In this arrangement, the light which is diffusely scattered becomes depolarized and passes on to the intensifier tube 22 with minimal attenuation. However, the specular reflections retain their polarization and are strongly attenuated.

Spectral filtering offers additional benefits. In spectral filtering the optical spectrum of the pulsed light source is compared with the spectrum of the welding arc. A spectral band is identified where the intensity ratio of pulsed light as arc light is greatest and it is only this bandwidth which is transmitted to the intensifer tube.

EXAMPLE

Figure 2A:
FIG. 2A is a photograph of a weld site taken using the present invention.
Figure 2B:
FIG. 2B is the same weld site without the aid of the present invention.

FIG. 2a shows a typical edge weld underway with two pieces of stainless steel material of about 1.25 mm thickness each. The welding arc was operating at about 50 Amperes and 12 volts. The flash lamp was discharging about 3.0 joules with a 3.0 microsecond pulse (width at half-intensity) at a 30 Hz pulse rate. The image tube gate width was about 2.5 microseconds and centered near the peak of the pulse for maximum signal response. FIG. 2b was taken from the same video recording and represents the same welding conditions, but without the pulsed illumination. The intensifier sensitivity was increased to achieve the best possible exposure with the available arc light, but the differences between the two cases are readily apparent.

The tungsten electrode is another feature that is easily recognized in both pictures. In the pulsed case, however, we note that the tungsten electrode is highlighted on the left side by the strobe lighting even despite the "white-hot" luminosity of this electrode. In the other case, the relative electrode brightness is very much stronger and saturates the video sensor. An interesting artifact (in both cases) is the reflection of the electrode in the welding pool, which is distorted by the convex curvature of the pool surface.

A xenon short-arc flashlamp (EG&G Model FX-132) was used for illumination. This lamp was powered by direct discharge of a 3.0 microfarad capacitor, which was charged between flashes by a d.c. power supply to a voltage level adjustable between 500 and 1500 volts. This allowed adjustment of discharge energy through the lamp over a range of 0.4–3.4 joules per pulse. Lamp firing was initiated by a separate trigger circuit to initiate gas ionization in the lamp with a trigger pulse of about ten kilovolts. The arc of the flashlamp was imaged onto the welding site with about 1:1 magnification using a pair of f/1.0 acrylic fresnel lenses positioned back to back.

The arrangement of FIG. 1 was adjusted to avoid intense specular reflection from the welding pool by rotating the viewing axis of the sensor out of that plane. A long, thin barrel extending from the sensor housing was used to support a single-element objective lens, which projected an image of the welding site onto the intensifier tube photocathode with an image magnification of about 2:1 and an aperature ratio of about f/30.

A standard 18-mm image intensifier tube, which is manufactured in quantity for military night vision goggles and rifle scopes, included a single-stage microchannel plate electron multiplier coupled to the photocathode and output phosphor screen with proximity-focused optics. The maximum luminous gain was about 12,000:1 and the photocathode spectral response covered the 450–850 nanometer range. The electronic shuttering feature was achieved by driving the tube photocathode with a voltage pulse, with zero volts representing the "off" condition and 50 volts representing "on". The image tube was coupled to the video camera with f/2.8 relay optics, although better coupling efficiency and image quality could be achieved with a fiberoptic coupler. The television camera was a Cohu Model 2850C, equipped with a one-inch vidicon tube and single-stage image intensifier with automatic gain control.

Spectral filters were used to restrict the bandpass to the 600–750 nanometer region. This is a region of relatively strong emission for the xenon lamp spectrum vs the spectrum of the welding plasma (primarily characteristic of the argon shield gas).

The strobe technique greatly enhances the contrast of the molten welding pool and sharply delineates the liquid/solid interface because (a) the molten metal is a strong specular reflector and reflects the directional strobe light away from the sensor field-of-view, and (b) because the diffuse scattering of strobe light from the solidified areas is very dominant over the luminosity of the welding plasma. This enhancement of the welding pool area should simplify the process of automatic tracking of pool position (for feedback position control) and for automatic sizing of the pool (for control of welding current).

The above description is given by way of example only and it should be understood that numerous modifications can be made without departing from the scope of the invention.

The embodiments of the invention in which an exclusive property or privilege is claimed are defined as follows:

1. A system for viewing a weld site obscured by an intense plasma or flame comprising:
    a pulsed light source providing an illumination beam for illuminating the weld site, the peak brightness of the light reflected from the weld site being greater than the brightness of the intense plasma or flame;
    an electronic image sensor for detecting a pulsed image of the illuminated weld site, said sensor operating as a high-speed shutter; and
    electronic means for synchronizing said shutter operation with said pulsed light source.

2. The system of claim 1 further comprising means for minimizing specular reflection from the weld site.

3. The system of claim 2 wherein said minimizing means comprises a polarizing filter positioned in front of the sensor.

4. The system of claim 3 further comprising a polarizing filter positioned in the illumination beam.

5. The system of claim 1 wherein said sensor comprises an intensifier tube and further comprising a video camera for receiving said detected pulsed image.

6. The system of claim 5 wherein said intensifier tube is positioned at an angle which excludes the angle of major specular reflection from the object.

7. The system of claim 1 wherein said pulsed light source comprises a xenon short-arc flashlamp.

8. The system of claim 1 wherein said pulsed light source comprises a pulsed laser.

9. The system of claim 1 wherein said pulsed light sources comprise a pulsed polarized laser.

10. The system of claim 1 further comprising preshuttering means positioned in front of the sensor.

11. A method of viewing a weld site obscured by an intense plasma or flame comprising the steps of:
    illuminating the weld site with a pulsed light source, the peak brightness of the light reflected from the weld site being greater than the brightness of the intense plasma or flame;
    detecting a pulsed image of the illuminated weld site on an electronic image sensor;
    operating said sensor as a high-speed shutter;
    and synchronizing said shuttering operation with said pulsed light source.

12. The method of claim 11 further comprising the step of minimizing the specular reflection from the weld site.

13. The method of claim 12 wherein the specular reflection from the weld site is minimized by polarizing said pulsed image prior to detection.

14. The method of claim 13 further comprising the step of polarizing the light from the pulsed light source.

15. The method of claim 11 wherein said sensor comprises an intensifier tube and further comprising the step of transferring said detected pulsed image to the photosensitive target of a video camera.

16. The method of claim 15 wherein said pulsed image is detected from an angle which excludes the angle of major specular reflection from the object.

17. The method of claim 11 wherein said pulsed light source comprises a xenon short-arc flashlamp.

18. The method of claim 11 wherein said pulsed light source comprises a pulsed laser.

19. The method of claim 11 wherein said pulsed light source comprises a pulsed polarized laser.

20. The method of claim 11 further comprising the step of pre-shuttering said pulsed image prior to detecting.

21. The system of claim 1 wherein said means for synchronizing said shutter operation with said pulsed light source enables said light source and said shutter for pulse width intervals less than or equal to 3.0 microseconds.

22. The apparatus of claim 21 having a discrimination ratio of at least 10,000:1.

23. The apparatus of claim 22 wherein said pulsed light source includes means for focusing light from said light source onto the weld site.

* * * * *